(12) United States Patent
Guillemont et al.

(10) Patent No.: US 10,526,338 B2
(45) Date of Patent: Jan. 7, 2020

(54) FUNCTIONALIZED PENTANOIC ACIDS FOR USE INFLUENZA VIRAL INFECTIONS

(71) Applicant: Janssen Sciences Ireland UC, Co Cork (IE)

(72) Inventors: Jérôme Émile Georges Guillemont, Andé (FR); Wendy Mia Albert Balemans, Kalmthout (BE); David Craig McGowan, Brussels (BE); Magali Madeleine Simone Motte, Louviers (FR); David Francis Alain Lançois, Louviers (FR); Emilie Marie Lambert, Rouen (FR)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 16/068,315

(22) PCT Filed: Jan. 5, 2017

(86) PCT No.: PCT/EP2017/050175
§ 371 (c)(1),
(2) Date: Jul. 5, 2018

(87) PCT Pub. No.: WO2017/118680
PCT Pub. Date: Jul. 13, 2017

(65) Prior Publication Data
US 2019/0023713 A1    Jan. 24, 2019

(30) Foreign Application Priority Data
Jan. 7, 2016 (EP) ..................... 16150457

(51) Int. Cl.
| C07D 487/04 | (2006.01) |
| C07D 471/04 | (2006.01) |
| A61K 31/519 | (2006.01) |
| A61K 31/437 | (2006.01) |
| A61P 31/16 | (2006.01) |
| A61K 31/444 | (2006.01) |
| A61K 31/506 | (2006.01) |
| A61K 45/06 | (2006.01) |
| A61P 31/12 | (2006.01) |

(52) U.S. Cl.
CPC .......... *C07D 487/04* (2013.01); *A61K 31/437* (2013.01); *A61K 31/444* (2013.01); *A61K 31/506* (2013.01); *A61K 31/519* (2013.01); *A61K 45/06* (2013.01); *A61P 31/12* (2018.01); *A61P 31/16* (2018.01); *C07D 471/04* (2013.01)

(58) Field of Classification Search
CPC .. A61K 31/437; A61K 31/519; C07D 471/04; C07D 487/04
See application file for complete search history.

(56) References Cited

FOREIGN PATENT DOCUMENTS

| WO | 2013019828 A1 | 2/2013 |
| WO | 2013184985 A1 | 12/2013 |
| WO | 2016037953 | 3/2016 |
| WO | 2016183120 A1 | 11/2016 |
| WO | 2016020526 A1 | 2/2017 |

OTHER PUBLICATIONS

International Search Report for Corresponding Application No. PCT/EP2017/050175, dated Feb. 28, 2017.

*Primary Examiner* — Susanna Moore

(57) ABSTRACT

The invention relates to compounds having the structure of formula (I) which can be used for the treatment of or against influenza infections.

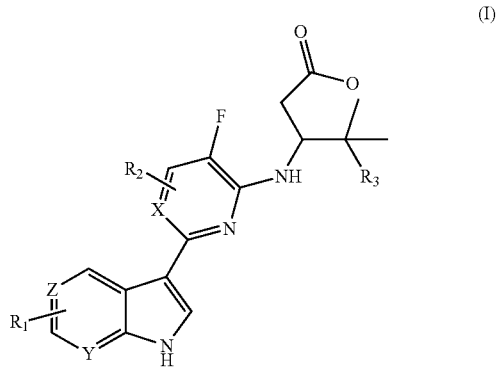

8 Claims, No Drawings

FUNCTIONALIZED PENTANOIC ACIDS FOR USE INFLUENZA VIRAL INFECTIONS

CROSS-REFERENCE TO RELATED APPLICATIONS

This application is a national phase entry of International Application No. PCT/EP2017/050175, filed on Jan. 5, 2017, which claims priority to EP Patent Application No. 16150457.6, filed Jan. 7, 2016, each of which is incorporated herein in its entirety.

Influenza is a serious public health problem with a high incidence in the human population resulting in regular large-scale morbidity and mortality. It is a highly contagious airborne disease that causes an acute febrile illness. Systemic symptoms vary in severity from mild fatigue to respiratory failure and death. According to the WHO the average global burden of annual epidemics may be on the order of 1 billion cases, 3-5 million cases of severe illness and 300,000-500,000 deaths annually. Every year, influenza viruses circulate in humans, typically affecting 5-20% of the population in all age groups, with this figure rising up to 30% during major epidemics. Rates of serious illness and death are highest among persons aged >65 years, children aged <2 years, and persons of any age who have medical conditions that place them at increased risk for complications from influenza, such as chronic heart, lung, kidney, liver blood or metabolic diseases, or weakened immune systems. Although deaths are infrequent among children, rates of hospitalization range from approximately 100 to 500 per 100,000 for children <5 years-old depending on the presence or absence of co-morbid conditions. Hospitalization rates among children aged <24 months are comparable to rates reported among persons aged >65 years.

In the US, annual influenza epidemics lead to approximately 30 million outpatient visits, resulting in medical costs of $10 billion annually. Lost earnings due to illness and loss of life represent a cost of over $15 billion annually and the total US economic burden of annual influenza epidemics amounts to over $85 billion.

Pathogens that cause influenza are negative sense, single-stranded RNA viruses, which belong to the family of Orthomyxoviridae. There are three types of influenza viruses: A, B and C. Influenza A viruses are the most common form, which can spread in mammals and birds. The subtypes of influenza A are named by the types of surface proteins hemagglutinin (H) and neuraminidase (N). There are 18 different hemagglutinin and 11 known neuraminidases. Current seasonal influenza viruses found in human are mainly H1N1 and H3N2 subtypes. Influenza B viruses are usually found only in humans. They are not divided into subtypes, but can be further broken down into different strains. Circulating influenza viruses are highly variable each year, and both influenza A and B cause seasonal epidemics all over the world. Influenza C viruses give much milder symptoms, which do not cause epidemics.

All three types of viruses have similar genome structures. The genome comprises 8 segments, encoding 9-11 proteins, depending on the type. Influenza A encodes 11 proteins, which includes the surface proteins (hemagglutinin (HA) and Neuraminidase (NA), the polymerase complex (PA, PB1 and PB2), nucleoprotein (NP), membrane proteins (M1 and M2), and other proteins (NS1, NS2, NEP). Among the three influenza virus types, influenza A has the highest rate of mutation. Influenza B evolves slower than A but faster than C. The segmented genome allows gene exchanging between different viral strains, which generate new variants of influenza viruses.

Influenza virus can be transmitted among humans by direct contact with infected individuals or virus-contaminated material. One can also be infected by inhalation of suspended virus droplets in the air. Those droplets are generated by coughing, sneezing or talking of infected individuals. Seasonal influenza is characterized by a sudden onset of high fever, cough (usually dry), headache, muscle and joint pain, severe malaise (feeling unwell), sore throat and runny nose. Cough can be severe and can last two or more weeks. Most people recover from fever and other symptoms within a week without requiring medical attention. But influenza can cause severe illness or death especially in people at high risk as mentioned above. The time from infection to illness, known as the incubation period, is about two days.

The most effective way to prevent the disease and/or severe outcomes from the illness is vaccination. Safe and effective vaccines are available and have been used for more than 60 years. Among healthy adults, influenza vaccines can provide reasonable protection. However, vaccination comes with several limitations. First, influenza vaccine may be less effective in preventing illness among the elderly, and may only reduce severity of disease and incidence of complications and deaths. In addition, influenza vaccination is most effective when circulating viruses are well-matched with vaccine viruses, and the success of vaccination is largely dependent on the good prediction of the most prevalent virus type of the season. Rapid and continual evolution of influenza viral strains through antigenic drift, coupled with the short-lived nature of vaccine-induced immune responses to current influenza vaccines, means that vaccination with seasonally appropriate strains is required every year for prevention.

The current treatment of influenza uses either direct antiviral drugs, or medicines that release the influenza-induced symptoms. There are two classes of influenza antiviral drugs available on the market: neuraminidase inhibitors and M2 channel inhibitors. Neuraminidase inhibitors oseltamivir or zanamivir are the primary antiviral agents recommended for the prevention and treatment of influenza. These are effective against both influenza type A and B viruses. Development of resistance to these antiviral drugs has been identified during treatment of seasonal influenza and in sporadic oseltamivir-resistant 2009 H1N1 virus, but the public health impact has been limited to date. M2 channel inhibitors, such as amantadine and rimantadine (amantadanes), are active against influenza A strains, but not influenza B strains. Adamantane resistance among circulating influenza A viruses increased rapidly worldwide beginning during 2003-2004. Therefore, amantadine and rimantadine are not recommended for antiviral treatment or chemoprophylaxis of currently circulating influenza A virus strains.

In 2009, the novel swine H1N1 strain caused an unexpected influenza pandemic as a result of reassortment of genes from human, pig, and bird's H1N1 viruses. This past pandemic, together with the ongoing circulation of highly pathogenic avian H5N1 strains and the recent emergence of the H7N9 virus, a new reassortant of avian origin isolated in China, and associated with severe respiratory disease with 40% of mortality, which could potentially adapt for human-to-human transmission, highlighted the vulnerability of the world population to novel influenza strains. Although vaccination remains the main prophylactic strategy for controlling influenza infection, to bridge the period before a new vaccine becomes available and to treat the severe influenza cases, as well as to counter the problem of viral resistance, a wider choice of anti-influenza drugs is required. Development of new influenza antivirals has therefore again become a high priority and an unmet medical need.

The current invention relates to a compound of formula (I) which can be used for the treatment of, or against viral influenza infections:

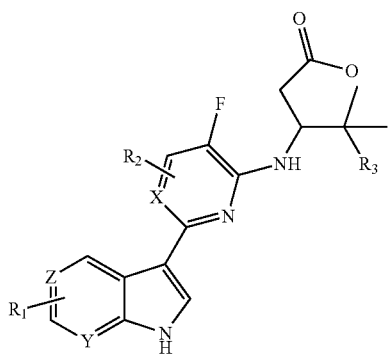

(I)

a stereo-isomeric form, a pharmaceutically acceptable salt, solvate or polymorph thereof, wherein Y is N, X is C, $R_1$ is halogen, $R_2$ is CN and $R_3$ is Het or $C_{2-6}$alkene;

or wherein

Y is N, X is N, $R_1$ is halogen, $R_2$ is H and $R_3$ is Het;

or wherein

Y is N, X is C or N, Z is C or N, $R_1$ is halogen or H, $R_2$ is H or CN, and $R_3$ is Het, $OCH_3$ or $CH_3$.

Preferably the compound according to the invention is the compound of formula (I) wherein $R_1$ is chloro or fluoro and $R_3$ is a heterocycle comprising one or more heteroatoms selected from N, O or S, said heterocycle may have 4, 5, 6 or 7 ring atoms and may optionally be substituted by $C_{1-6}$ alkyl.

One of the most preferred compounds according to the invention has the structural formula (II):

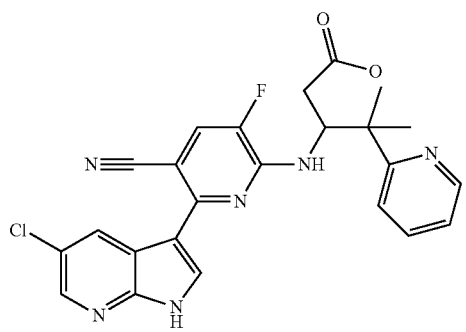

(II)

Most preferred compound according to the invention has the following structure (III):

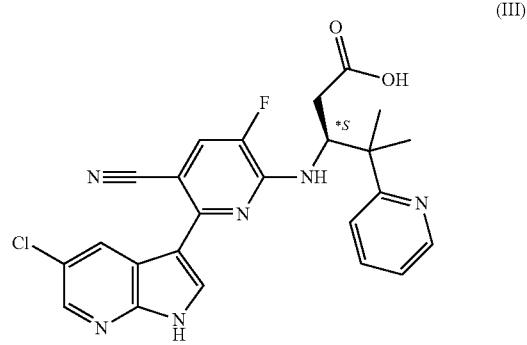 [SMILES: CC(C)(c1ccccn1)[C@H](CC(=O)O)Nc1nc(-c2c[nH]c3ncc(Cl)cc23)c(C#N)cc1F]

(III)

Part of the invention is also a pharmaceutical composition comprising a compound of formula (I), (II) or (III), a stereo-isomeric form, a pharmaceutically acceptable salt, solvate or polymorph thereof together with one or more pharmaceutically acceptable excipients, diluents or carriers.

The pharmaceutical composition may also include additional therapeutic agents like another antiviral agent or an influenza vaccine, or both.

To the invention also belongs a compound of formula (I), (II) or (III), a stereo-isomeric form, a pharmaceutically acceptable salt, solvate or polymorph thereof or a pharmaceutical composition for use as a medicament.

Additionally the invention relates to a compound of formula (I), (II) or (III), a stereo-isomeric form, a pharmaceutically acceptable salt, solvate or polymorph thereof or a pharmaceutical composition for use in the treatment of influenza.

So part of the invention is the use of a compound represented by the following structural formula (I)

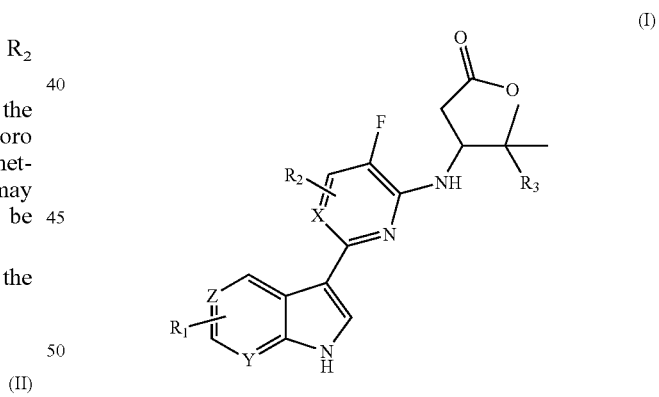

(I)

a stereo-isomeric form, a pharmaceutically acceptable salt, solvate or polymorph thereof, wherein Y is N, X is C, $R_1$ is halogen, $R_2$ is CN and $R_3$ is Het or $C_{2-6}$alkene;

or wherein

Y is N, X is N, $R_1$ is halogen, $R_2$ is H and $R_3$ is Het;

or wherein

Y is N, X is C or N, Z is C or N, $R_1$ is halogen or H, $R_2$ is H or CN and $R_3$ is Het, $OCH_3$ or $CH_3$ for inhibiting the replication of influenza virus(es) in a biological sample or patient.

Said use may also comprise the co-administration of an additional therapeutic agent, wherein said additional therapeutic agent is selected from an antiviral agent or influenza vaccine, or both.

The term "heterocycle" (Het) refers to molecules that are saturated or partially saturated comprising one or more heteroatoms selected from N, O or S, in particular from N and S. Said heterocycle may have 4, 5, 6 or 7 ring atoms. In particular, said heterocycle may have 5 or 6 ring atoms.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess. Said mixture may contain all diastereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

PREPARATION OF COMPOUNDS ACCORDING TO THE INVENTION

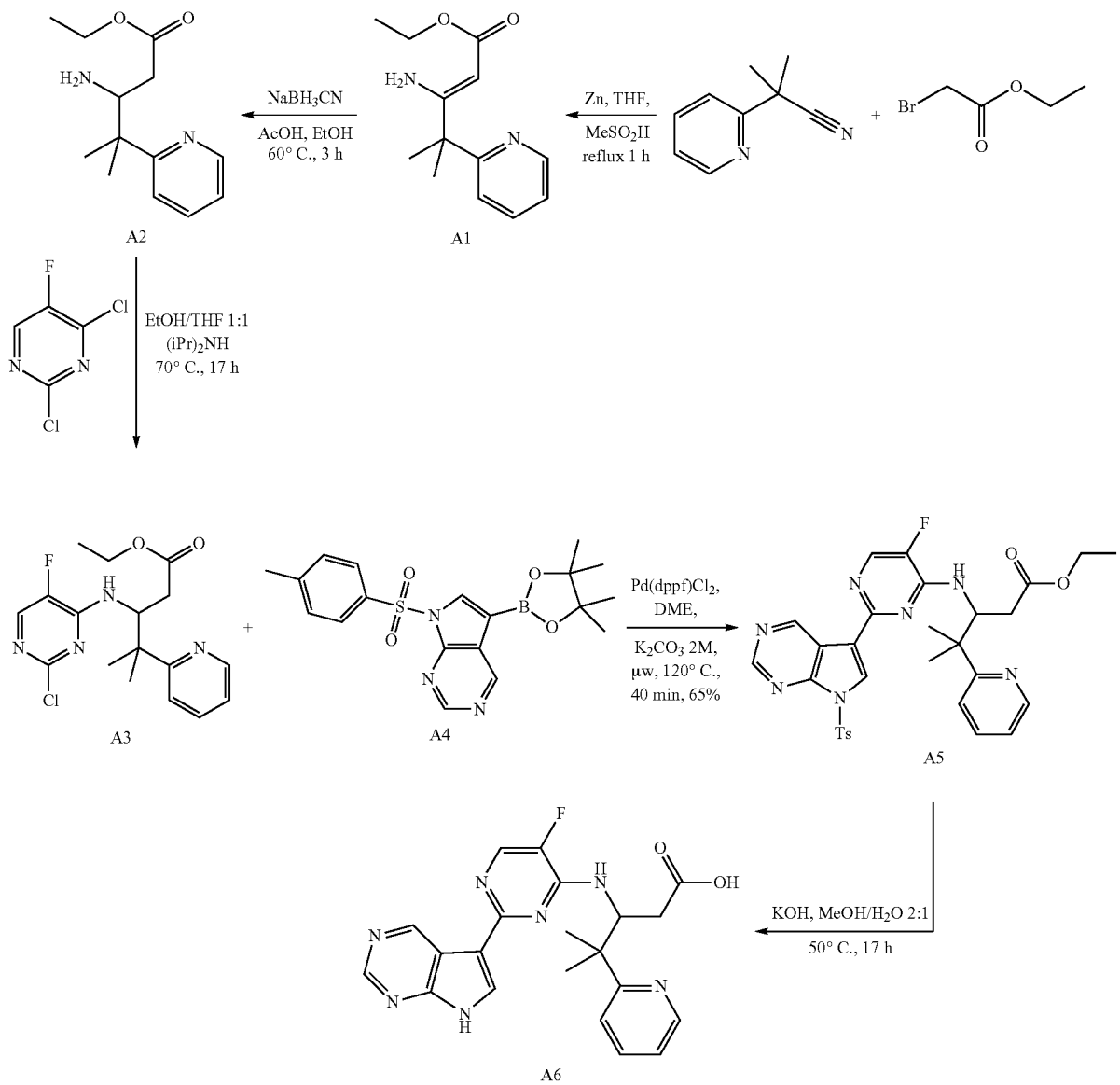

Preparation of Intermediate A1

Methanesulfonic acid (1.3 mL, 20.4 mmol) was added to a suspension of activated Zn (17.4 g, 267 mmol) in THF (150 mL) at rt. The reaction mixture was stirred at reflux for 15 minutes and a solution of 2-methyl-2-(2-pyridyl)propanenitrile [CA-81039-18-1] (7.8 g, 55.3 mmol) in THF (50 mL) was added. Then a solution of ethylbromoacetate (17.8 mL, 160 mmol) in THF (50 mL) was added dropwise over 45 min at reflux. The reaction mixture was stirred at reflux for 1 h. An aqueous saturated solution of NaHCO$_3$ was added and washed with EtOAc. The combined organic layers were dried over MgSO$_4$, filtered and concentrated. The residue was purified by preparative LC (irregular SiOH, 15-40 μm, GraceResolv, mobile phase) using cyclohexane/EtOAc gradient. Pure fractions were collected and evaporated to give 12.8 g of intermediate A1 as a colorless liquid (quant).

Preparation of Intermediate A2

NaBH$_3$CN (1.9 g; 30.7 mmol) was added to a solution of intermediate A1 (6 g; 25.6 mmol) in EtOH (300 mL) and AcOH (28 mL). The resulting mixture was heated at 60° C. for 3 h. An aqueous saturated solution of NaHCO$_3$ and then, the aqueous layer was extracted with EtOAc. The combined organic layers were dried over MgSO$_4$, filtered and concentrated in vacuo to give 3.6 g of intermediate A2 (59%) as a yellow oil.

Preparation of Compound A3

A solution of the intermediate A2 (1.8 g, 7.62 mmol), 2,4-dichloro-5-fluoro-pyrimidine (31.15 g, 6.9 mmol) and diisopropylamine (7.6 mL, 41.55 mmol) was stirred and heated at 70° C. for 17 h. Water was added to the reaction mixture and then the aqueous layer was extracted twice with EtOAc. Organic layers were collected, dried over MgSO$_4$, filtered and evaporated to obtain the crude product. The crude was purified via silica gel chromatography (irregular SiOH, 15-40 μm, 80 g GraveREsolv), using Heptane/EtOAc gradient. Fractions were pooled and the solvent removed to afford A3, 2.08 g, 65% of a colorless oil.

Preparation of Compound A5

A solution of intermediate A4 [CAS-934178-97-9] (273 mg, 0.7 mmol), intermediate A3 (275.9 mg, 0.8 mmol) and K$_2$CO$_3$ (1 mL, 2 M, 2.1 mmol) in DME (3 mL) was purged with N$_2$ flow for 5 min and then Pd(dppf)Cl$_2$ (56 mg, 0.07 mmol) was added. The resulting mixture was stirred and heated at 120° C. using a singlemode microwave (Biotage initiator60) with a power output ranging from 0 to 400 W for 40 min. The mixture was poured out into water and DCM, the organic layer was separated with an hydrophobic frit and evaporated till dryness. Purification was carried out by flash chromatography over silica gel (irregular SiOH, 15-35 μm, 40 g, Heptane/EtOAc from 100/0 to 80/20). Pure fractions were collected and evaporated to intermediate A5 as colorless oil, 0.270 g, 65%.

Preparation of Compound A6

KOH (248.4 mg, 4.4 mmol) was added to a solution of A5 (270 mg, 0.4 mmol) in a mixture of MeOH/Water ([2:1], 0.75 mL]. The resulting solution was stirred and heated at 50° C. for 17 h. The solution was cooled down to room temperature. DCM (2 mL) was added, the mixture was neutralized with HCl 3N. The layers were separated through an hydrophobic frit. The organic layer was dried over MgSO$_4$, filtered and evaporated. Purification was performed via preparative reverse phase (Stationary phase: X-Bridge-C18 5 μm 30*150 mm, Mobile phase: Gradient from 90% NH$_4$HCO$_3$ 0.5%, 10% ACN to 50% NH$_4$HCO$_3$ 0.5%, 50% ACN). Pure fractions were collected and evaporated. The resulting solid was dried under reduced pressure at 40° C. for 5 h to give compound A6, 0.11 g, 4.6%. mp° C.: 158.

$^1$H NMR (500 MHz, DMSO-d$_6$) δ ppm 1.30 (s, 3 H) 1.38(s, 3 H) 2.01 (dd, J=15.4 Hz, 2.8 Hz, 1H) 2.38 (m, 2H) 5.65 (m, 1H) 7.23 (dd, J=7.9 Hz, 5.0 Hz, 1 H) 7.44 (d, J=7.9 Hz, 1 H) 7.73 (td, J=8.9 Hz 1.9 Hz, 1 H) 8.04 (br, d, J=8.2 Hz, 1 H) 8.13 (d, J=4.1 Hz, 1H) 8.16 (s, 1H) 8.76 (d, J=3.8 Hz, 1H) 8.85 (s, 1H) 10.2 (s, 1H)

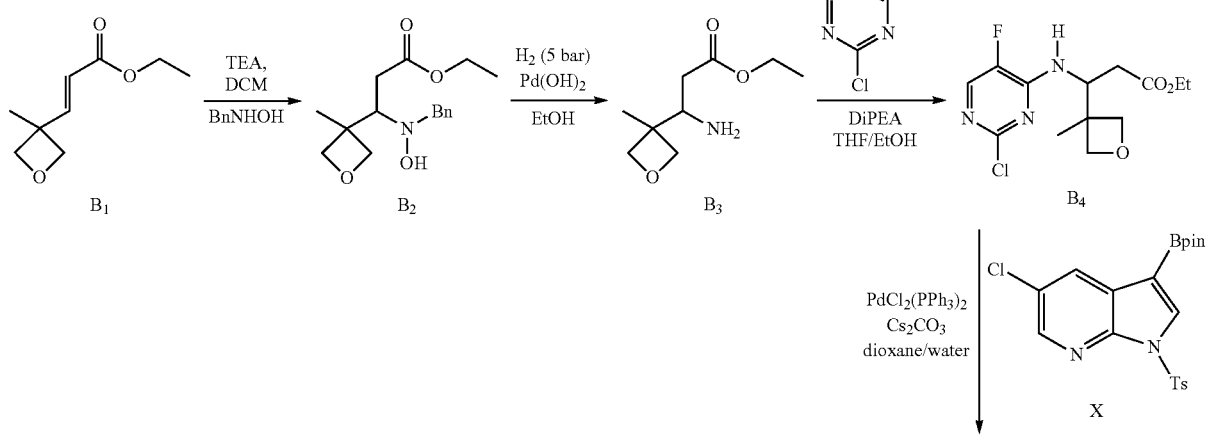

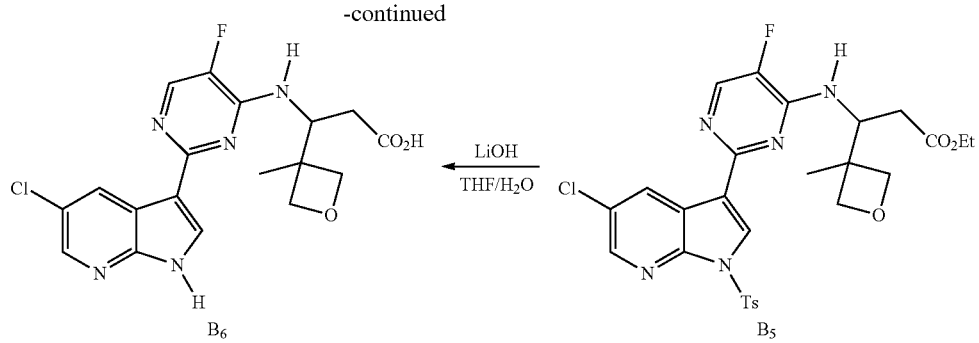

Preparation of Intermediate B2

Under nitrogen, TEA (0.87 mL, 6.3 mmol) was added to a mixture of B1 [1123787-64-3] (710 mg, 4.2 mmol) and N-Benzylhydroxylamine hydrochloride (0.87 g, 5.4 mmol) in dry DCM (27 mL) and stirred at rt overnight. The mixture was concentrated to give a residue which was purified by preparative LC (Stationary phase: Interchim, 30 μm, 24 g, Mobile phase gradient: Heptane/EtOAc from 90/10 to 60/40) to give 561 mg (46%) of B2 as a colorless oil.

Preparation of Intermediate B3

In a stainless bomb, a solution of B2 (561 mg, 1.9 mmol) and Pearlman catalyst (537 mg; 38 μmol) in EtOH (22 mL) was stirred under an atmosphere of H2 (5 bar) overnight. The mixture was diluted with AcOEt and filtered through a pad of Celite®. The solvent was removed in vacuo to give B3 (311 mg, colorless oil, 87%).

Preparation of Intermediate B4

2,4-dichloro-5-fluoro-pyrimidine (0.138 g; 0.828 mmol), DIPEA (0.71 mL; 4.1 mmol), B3 (0.155 g; 0.828 mmol) in THF (2.1 mL) and EtOH (2.1 mL) were heated at 90° C. for 18 hours in a sealed tube. EtOAc was added and washed twice with brine. The organic layer was dried over MgSO4, filtered and evaporated in vacuo to give a colorless oil which was purified by preparative LC (regular SiOH 30 μm, 24 g Interchim, mobile phase gradient: from Heptane/EtOAc 80/20 to 50/50) to give 170 mg of B4 as a white solid (65%).

Preparation of Intermediate B5

Under N2, in a sealed tube, a mixture of compound X (141 mg; 0.29 mmol, 90% purity), B4 (85 mg; 0.27 mmol) and Cs2CO3 (0.31 g; 0.94 mmol) in 1,4 dioxane (2.3 mL) and water (0.72 mL) was degassed with N2 for 5 min. PdCl2(PPh3)2 (19 mg; 27 μmol) was added and the reaction mixture was degassed again with N2 for 2 min. The reaction mixture was heated at 90° C. for 1 h30.The reaction mixture was cooled down to rt. DCM and brine were added to reaction mixture. The aqueous layer was extracted with DCM. The combined organic layers were washed dried over MgSO4, filtered off and concentrated to dryness to afford a residue which was purified by preparative LC (regular SiOH 30 μm, 12 g, Interchim, mobile phase gradient: from Heptane/EtOAc 85/15 to 60/40) to give 89 mg of B5 as a white solid (57%).

Preparation of Compound B6

LiOH monohydrate (128 mg, 3.1 mmol) was added to a mixture of B5 (90 mg, 0.15 mmol) in water (0.29 mL) and THF (0.84 mL). The mixture was stirred for 18 h at 60° C. The solution was neutralized with HCl 3N (caution: preferably stay at basic pH, around 7-8 at best) and the solvent was evaporated in vacuo to give 250 mg of a residue which was purified via Reverse phase (Stationary phase: X-Bridge-O18 5 μm 30*150 mm, Mobile phase: Gradient from 90% (aq. NH4HCO3 0.5%), 10% MeCN to 50% (aq. NH4HCO3 0.5%), 50% MeCN). Fractions containing pure compound were evaporated and the solid obtained was freeze-dried in MeCN/H2O to give B6 (18 mg, white solid, 29%). LC-MS Mass Found [M+H]+=406.1. Rt(min)=1.78 (method A)

$^1$H NMR (500 MHz, DMSO-$d_6$) δ ppm 1.39 (s, 3H), 2.45-2.55 (m, 1H), 2.58 (dd, J=15.8, 10.4 Hz, 1 H), 4.10 (d, J=5.7 Hz, 1 H), 4.19 (d, J=6.0 Hz, 1 H), 4.51 (d, J=6.0 Hz, 1 H), 4.73 (d, J=5.7 Hz, 1 H), 5.18-5.30 (m, 1H), 7.77 (br s, 1H), 8.18(d J=4.1 Hz, 1 H), 8.19 (s, 1H), 8.28 (d, J=2.2 Hz, 1 H), 8.81 (d, 2.2 Hz, 1 H), 12.35 (br s, 2H)

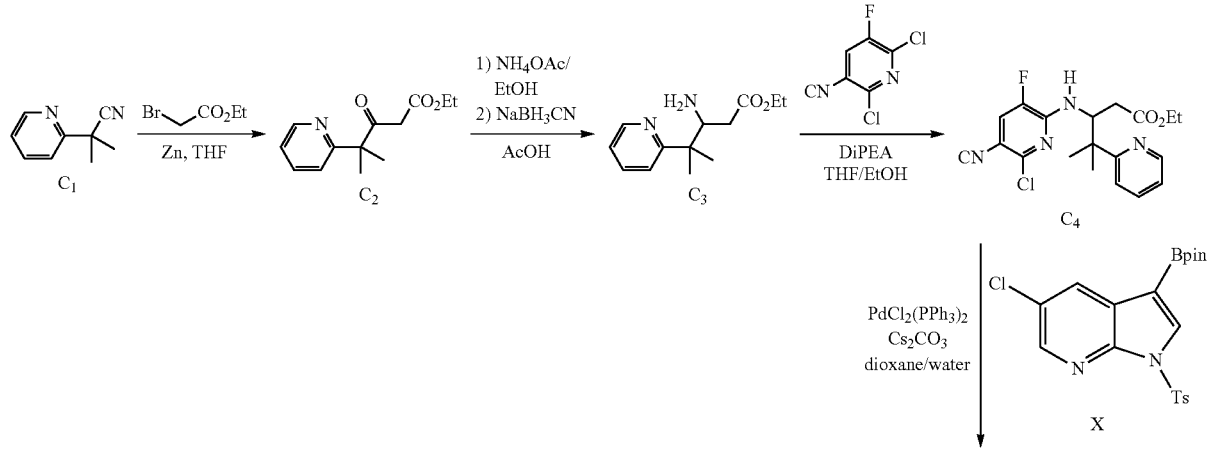

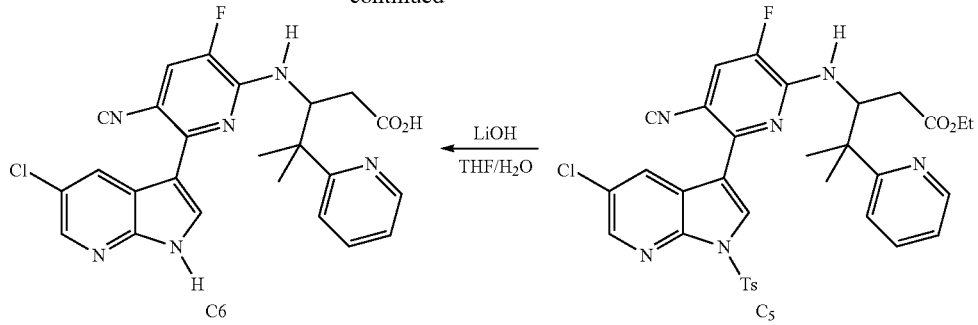

Preparation of Intermediate C2

Methanesulfonic acid (0.675 mL, 10.4 mmol) was added to a suspension of activated Zn (8.94 g, 137 mmol) in THF (60 mL) at rt. The reaction mixture was stirred at reflux for 15 minutes and a solution of compound C1 [J. Org. Chem. 2013, 78, 762-769] (4.00 g, 27.4 mmol) in THF (20 mL) was added. Then a solution of ethylbromoacetate (9.14 mL, 82.1 mmol) in THF (40 mL) was added dropwise at reflux. The reaction mixture was stirred at reflux for 1 h. An aqueous solution of saturated $NaHCO_3$ was added and the mixture was filtered over celite. The filtrate was extracted with ethyl acetate (2×15 mL), dried over $Na_2SO_4$, filtered and concentrated under reduced pressure. The residue was purified by preparative LC (irregular SiOH, 40-63 µm, Fluka, liquid loading (DCM), mobile phase: DCM 100%) to give 3.6 g of intermediate C2 as a yellow liquid (56%).

Preparation of Intermediate C3

To a mixture of intermediate C2 (2.3 g; 5.67 mmol) in EtOH (50 mL) was added $NH_4OAc$ (2.19 g; 28.3 mmol). The reaction mixture was stirred at 80° C. for 18 h. The mixture was cooled to rt and AcOH (6.17 mL; 108 mmol) and a commercial solution of $NaBH_3CN$ 1M in THF (85 mL; 85.0 mmol) were added and the reaction mixture was heated at 60° C. for 4 h. An aqueous saturated solution of $NaHCO_3$ and EtOAc were added. The aqueous layer was extracted with EtOAc (twice). The combined organic layers were dried over MgSO4, filtered and evaporated in vacuo. The residue was purified by preparative LC (irregular SiOH 15-40 µm, 80 g GraceResolv, mobile phase gradient: from DCM/MeOH/aq$NH_3$ 100/0/0 to 90/10/1) to give 1.63 g of intermediate C3 (quant).

Preparation of Intermediate C4

Intermediate C3 (1.80 g; 7.62 mmol), 2,6-dichloro-3 cyano-5 fluoropyridine (1.46 g; 762 mmol), DIPEA (6.65 mL; 38.1 mmol) in THF (50 mL) and EtOH (50 mL) were heated at 90° C. for 18 h.

An extra amount 2,6-dichloro-3 cyano-5 fluoropyridine (0.145 g; 0.762 mmol) was added and the reaction mixture was stirred at 90° C. for 4 h. Water and brine were added. The aqueous layer was extracted with EtOAc (twice). The combined organic layers were dried over MgSO4, filtered, evaporated in vacuo and purified by preparative LC (irregular SiOH 15-40 µm, 120 g GraceResolv, liquid loading (DCM), mobile phase gradient: from heptane/EtOAc: 90/10 to 60/40) to give 1.76 g of intermediate C4 (59%).

Preparation of Compound C5

Under $N_2$, in a sealed tube, a mixture of compound X [CA-866546-11-4] (1.22 g; 2.83 mmol), intermediate C4 (0.850 g; 2.18 mmol) and $Cs_2CO_3$ (2.48 g; 7.61 mmol) in dioxane (15 mL) and $H_2O$ (6 mL) was degassed with $N_2$ for 5 min. $PdCl_2(PPh_3)_2$ (153 mg; 0.217 mmol) was added and the reaction mixture was degassed again with $N_2$ for 2 min. The reaction mixture was heated at 90° C. for 2 h.

The reaction mixture was cooled down to rt. EtOAc and brine were added to reaction mixture. The aqueous layer was extracted with EtOAc. The combined organic layers were washed with brine, dried over MgSO4, filtered off, evaporated in vacuo and purified by preparative LC (irregular SiOH 15-40 µm, 40 g Graceresolv, dry loading over SiOH, mobile phase gradient: from Heptane/EtOAc 90/10 to 50/50) to give 230 mg of compound C5 as a solid (14%).

Preparation of Compound C6

In a sealed tube, to a solution of compound X (300 mg; 0.227 mmol) in THF (2 mL) and $H_2O$ (0.7 mL) was added LiOH monohydrate (68 mg; 1.59 mmol). The reaction mixture was stirred at 25° C. overnight.

The reaction mixture was evaporated and purified by preparative LC (irregular SiOH 15-40 µm, 40 g GraceResolv, dry loading (over SiOH), mobile phase gradient: from DCM/MeOH 100/0 to 80/20) 80 mg of impure compound. DCM was added to impure compound and the solid was filtered and rinced with DCM then acetone. The solid was purified again by preparative LC (irregular SiOH 15-40 µm, 24 g GraceResolv, dry loading over SiOH, mobile phase gradient: from DCM/MeOH 100/0 to 93/7) to give 75 mg of C6 (69%), mp=256.46° C.

$^1$H NMR (500 MHz, DMSO-$d_6$) δ ppm 1.34 (s, 3 H) 1.37 (s, 3 H) 2.17 (br d, J=15.1 Hz, 1 H) 2.50 (m, 1 H) 5.58 (br t, J=9.5 Hz, 1 H) 7.18 (t, J=6.6 Hz, 1 H) 7.39 (br d, J=7.9 Hz, 1 H) 7.67 (t, J=7.6 Hz, 1 H) 7.64-7.81 (br s, 1 H) 7.85 (br d, J=11.4 Hz, 1 H) 8.32 (s, 1 H) 8.37 (s, 1 H) 8.47 (br d, J=3.8 Hz, 1 H) 9.13 (br s, 1 H) 12.08 (br s, 1 H) 12.47 (s, 1 H)

LC-MS Mass Found [M+H]+=479.0. Rt(min)=2.39 min (method A)

Separation of Pure Isomers of C6

Compound C6 was purified via chiral SFC (Stationary phase: CHIRALCEL AD (5.0 cm I.D×25 cmL), mobile phase: 70% $CO_2$, 30% EtOH. Then each isomer was re-purify by chiral HPLC (Stationary phase: CHIRALPAK AD, mobile phase: 70% Hexane, 30% EtOH, 0.1% AcOH to give 30 mg of enantiomer 1 called [(−)-C6]; mp° C.=231.52, [α]$^{25°}$ $^{c}_{589\ nm}$=−37.1 and 35 mg of enantiomer 2 called [(+)-C6], m=35 mg; mp° C.=229.28, [α]$^{25°}$ $^{c}_{589\ nm}$=41.0.

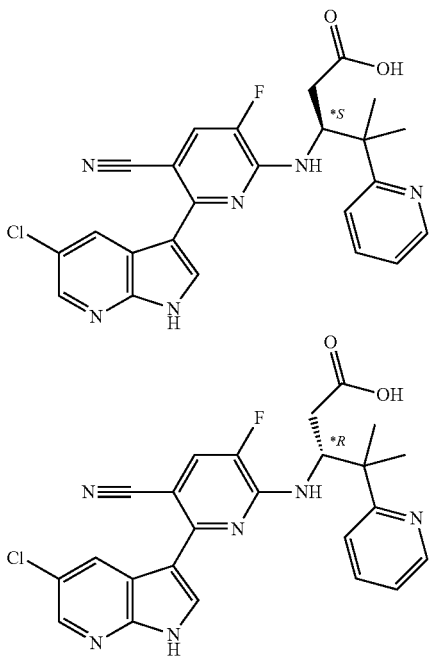

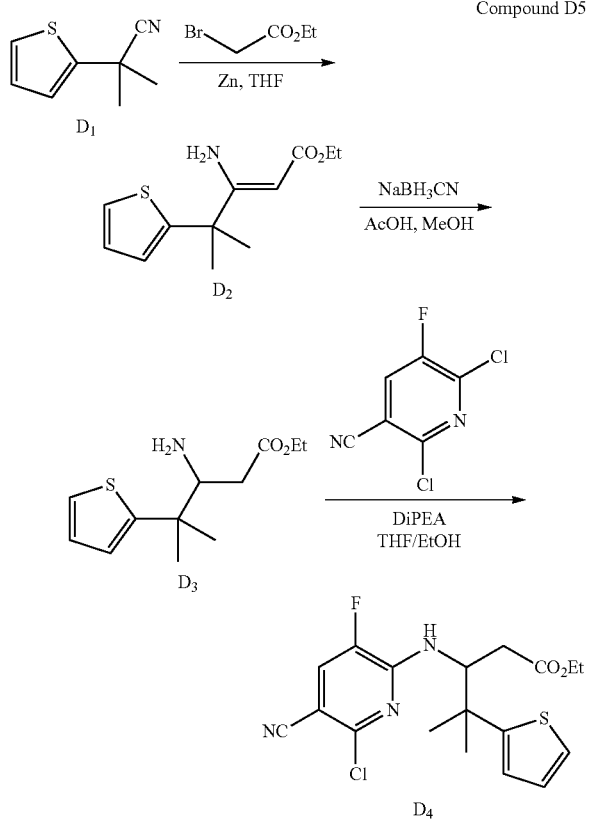

Preparation of Intermediate D2

A suspension of activated Zn (13 g; 198 mmol) in dry THF (100 mL) was heated under reflux then 1,2-dibro-moethane (855 µL; 9.92 mmol) and fews drops of ethylbromoacetate were added. After 20 min at reflux, a solution of compound D1 (5 g; 33.1 mmol) in dry THF (100 mL) was added in one portion. Ethylbromoacetate (15 mL; 132 mmol) was added dropwise over 50 min. The mixture was stirred at 70° C. for 20 min then cooled down to rt then treated with an aqueous solution of NaHCO$_3$ and filtered through a pad of celite. The filtrate was extracted with EtOAc (twice). The combined organic layers were dried over MgSO$_4$, filtered and concentrated in vacuo to give 10 g of crude D2.

The crude was purified by preparative LC (Regular SiOH 30 µm, 200 g Interchim, liquid loading (DCM), mobile phase gradient: from Heptane/EtOAc 100:0 to 80:20). The fractions containing product were combined and the solvent was removed in vacuo to give 5.7 g of intermediate D2 (72%) as a colorless oil.

Preparation of Intermediate D3

NaBH$_3$CN (1.5 g; 23.9 mmol) was added to a solution of intermediate D2 (4.7 g; 19.6 mmol) in MeOH (118 mL) and AcOH (12 mL). The resulting mixture was stirred at rt overnight. The mixture was quenched by addition of water and the solvent was evaporated in vacuo. The resulting mixture was basified by addition of a solution of NaOH (1N) pH=10-14, then extracted with DCM (twice). The combined organic layers were washed with brine, dried over MgSO$_4$, filtered and concentrated in vacuo to give 4.6 g of intermediate D3 (97%) as a colorless oil.

Preparation of Intermediate D4

A mixture of 2,6-dichloro-3 cyano-5 Fluoropyridine (396 mg; 2.07 mmol), intermediate D3 (500 mg; 2.07 mmol) and DIPEA (543 µL; 3.11 mmol) in THF (10 mL) and EtOH (10 mL) was stirred at 90° C. for 2 h. The mixture was transferred in sealed tube and 2,6-dichloro-3 cyano-5 Fluoropyridine (396 mg; 2.07 mmol) was added, the resulting mixture was stirred at 90° C. for 16 h. 2,6-dichloro-3 cyano-5 Fluoropyridine (396 mg; 2.07 mmol) and DIPEA (543 µL; 3.11 mmol) was added and the mixture was stirred at 90° C. for 6 h. The mixture were concentrated until dryness and was purified by preparative LC (Irregular SiOH 15-40 µm, 50 g Merck, mobile phase gradient: from Heptane/DCM 80:20 to 0:100). The fractions containing product were combined and the solvent was removed in vacuo to give 224 mg intermediate D4 as a yellow solid (40%).

Compound D5 was prepared in the same way as the racemate compound C6 starting from compound X and intermediate D4

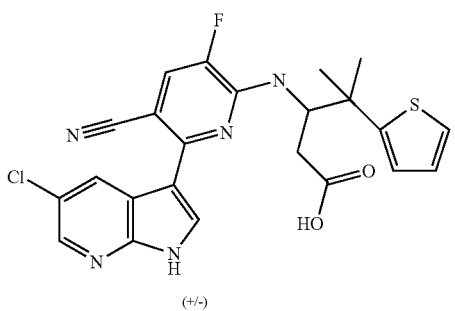 [SMILES: CC(C)(c1cccs1)C(CC(=O)O)Nc1nc(-c2c[nH]c3ncc(Cl)cc23)c(C#N)cc1F]

(+/−)

$^1$H NMR (500 MHz, DMSO-d$_6$) δ ppm 1.18 (s, 3 H) 1.37 (s, 3 H) 2.26 (br d, J=15.1 Hz, 1 H) 2.57-2.67 (m, 1 H) 5.35 (br t, J=9.9 Hz, 1 H) 6.90-6.95 (m, 2 H) 7.34 (dd, J=4.9, 1.4 Hz, 1 H) 7.67-7.86 (br s, 1 H) 7.88 (d, J=11.4 Hz, 1 H) 8.31 (s, 1 H) 8.36 (d, J=2.5 Hz, 1 H) 9.03 (d, J=2.2 Hz, 1 H) 12.17

(br s, 1H) 12.48 (br s, 1 H). LC-MS Mass Found [M+H]+=484.1. Rt(min)=2.55 (method A), mp° C.=280.59.

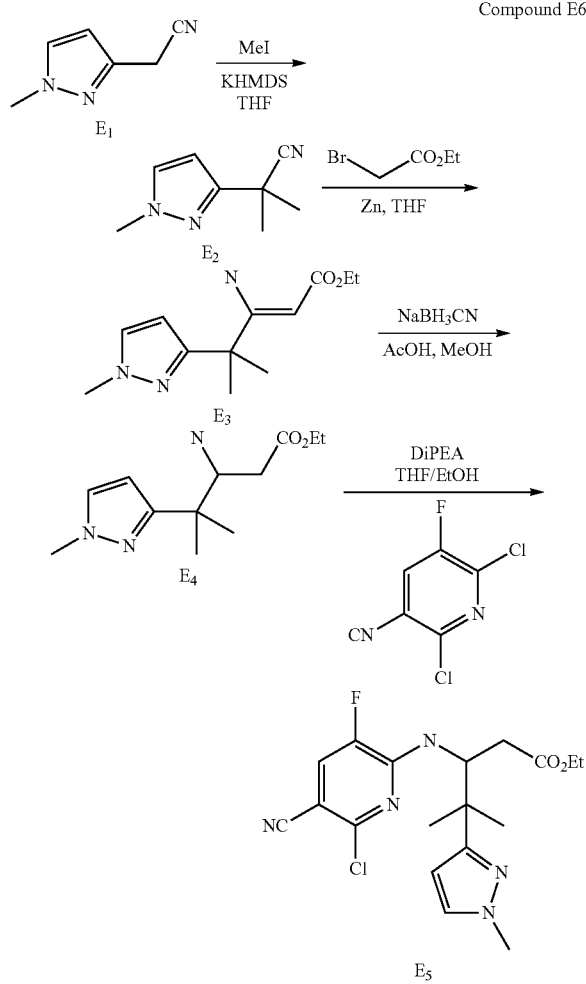

Preparation of Intermediate E2 tBuOK (14.5 g; 130 mmol) was added by portions to a solution of compound E1 [1142927-97-6] (6.28 g; 51.8 mmol) and 18-crown-6 (2.1 g; 7.8 mmol) in THF (200 mL) at 0° C. The mixture was stirred at 0° C. for 15 min before the slow addition of iodomethane (9.7 mL; 156 mmol). The mixture was stirred at 0° C. for 15 min, then at rt for 16 h. The reaction mixture was quenched with an aqueous solution of NH$_4$Cl and extracted with EtOAc (twice). The combined organic layers were washed with brine, dried over MgSO$_4$, filtered and evaporated in vacuo to give 8 g of crude E2

The crude was purified by preparative LC (Regular SiOH 30 μm, 300 g Interchim, dry loading (on Silica), mobile phase gradient: from Heptane/EtOAc 80/20 to 0/100) to give 6 g of intermediate E2 as a colorless oil (78%).

Preparation of Intermediate E3

A suspension of activated Zn (10.5 g; 161 mmol) and methanesulfonic acid (800 μL; 12.3 mmol) in THF (65 mL) was heated under reflux for 15 min then intermediate E2 (4.8 g; 32.2 mmol) in THF (15 mL) was added. Then ethylbromoacetate (10.7 mL; 96.7 mmol) in THF (50 mL) was added dropwise over 45 min. The mixture was stirred at reflux for 1 h then cooled down to rt then treated with an aqueous saturated solution of NaHCO$_3$, filtered through a pad of celite and washed with EtOAc. The layers were separated. The organic layer was washed with brine, dried over MgSO$_4$, filtered, concentrated in vacuo and purified by preparative LC (Regular SiOH 30 μm, 300 g, Interchim, dry loading (on Silica), mobile phase gradient: from Heptane/EtOAc 80/20 to 50/50) to give 6.37 g of intermediate E3 as a colorless oil (83%).

Preparation of Intermediate E4

NaBH$_3$CN (1.86 g; 29.6 mmol) was added to a solution of intermediate E3 (2.94 g; 12.4 mmol) in MeOH (80 mL) and AcOH (15 mL). The resulting mixture was stirred at rt for 56 h. The mixture was quenched by addition of water and the solvent was evaporated in vacuo. The resulting mixture was basified by addition of a solution of NaOH (1N) until pH=10-14, then extracted with DCM (twice). The combined organic layers were washed with brine, dried over MgSO$_4$, filtered and concentrated in vacuo to give 2.9 g of crude E4.

The crude was purified by preparative LC (Regular SiOH 15-30 μm, 80 g Interchim, mobile phase gradient: from DCM/MeOH: 100/0 to 90/10) to give 2.09 g of intermediate E4 as a colorless oil (70%).

Preparation of Intermediate E5

2,6-dichloro-3 cyano-5 Fluoropyridine (851 mg; 4.46 mmol), DIPEA (3.9 mL; 22.3 mmol), intermediate E4 (1 g; 4.18 mmol) in THF (10 mL) and EtOH (10 mL) were heated at 90° C. for 16 h in a sealed tube. Solvents were evaporated. Water was added. The aqueous layer was extracted with DCM (3 times). The organic layer was dried over MgSO$_4$, filtered and evaporated in vacuo and was purified by preparative LC (Irregular SiOH 15-40 μm, 50 g Merck, dry loading (on SiOH), mobile phase gradient: from Heptane/EtOAc: 90/10 to 50/50) to give 843 mg of intermediate E5 as a gum (48%).

Compound E6

Compound E6 was prepared in the same way as the racemate compound C6 starting from compound X and intermediate E5

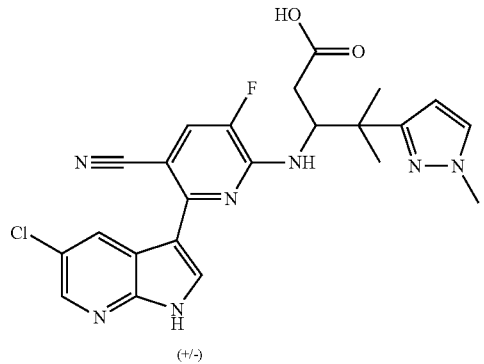 [SMILES: Cn1ccc(C(C)(C)C(CC(=O)O)Nc2nc(-c3c[nH]c4ncc(Cl)cc34)c(C#N)cc2F)n1]

(+/-)

$^1$H NMR (400 MHz, DMSO-d$_6$) δ ppm 1.16 (s, 3 H) 1.26 (s, 3 H) 2.35-2.56 (m, 2 H) 3.73 (s, 3 H) 5.24 (br t, J=9.4 Hz, 1 H) 6.06 (d, J=2.0 Hz, 1 H) 7.46-7.60 (m, 1 H) 7.53 (d, J=1.5 Hz, 1 H) 7.85 (d, J=11.1 Hz, 1 H) 8.31 (br s, 1 H) 8.34 (d, J=2.5 Hz, 1 H) 9.03 (d, J=2.5 Hz, 1 H) 12.07 (br s, 1 H) 12.45 (br s, 1 H). LC-MS Mass Found [M+H]+=484.1. Rt(min)=2.55 (method A), mp° C.=288.09.

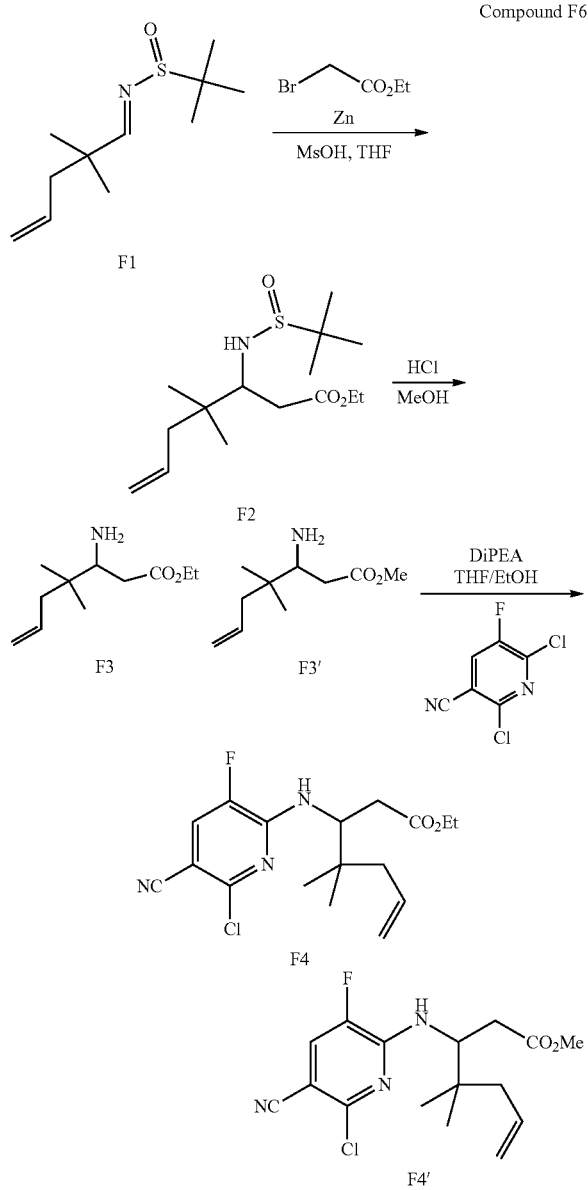

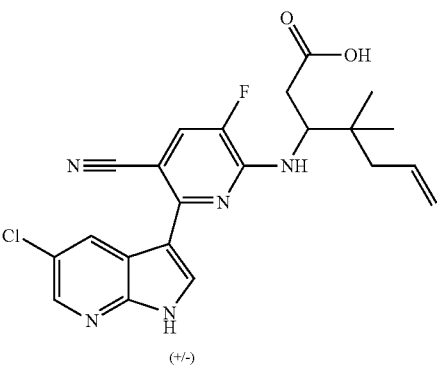 [SMILES: C=CCC(C)(C)C(CC(=O)O)Nc1nc(-c2c[nH]c3ncc(Cl)cc23)c(C#N)cc1F]

Preparation of Intermediate F2

A suspension of activated Zn (1.41 g; 21.6 mmol) and Methanesulfonic acid (107 μL; 1.65 mmol) in dry THF (10 mL) was heated under reflux for 15 min then compound F1 [856659-63-7] (930 mg; 4.32 mmol) in dry THF (5 mL) was added. Then ethylbromoacetate (1.4 mL; 13.0 mmol) in dry THF (5 mL) was added dropwise over 10 min. The mixture was stirred at reflux for 1 h then cooled down to rt, then treated with an aqueous saturated solution of NaHCO₃, filtered through a pad of celite and washed with EtOAc. The layers were separated. The organic layer was washed with brine, dried over MgSO₄, filtered, concentrated in vacuo and purified by preparative LC (Irregular SiOH 15-40 μm, 40 g, Grace, dry loading (on SiOH), mobile phase gradient: from Heptane/EtOAc 90/10 to 50/50) to give 672 mg of intermediate F2 as a colorless oil (51%).

Preparation of Intermediate F3/F3'

A mixture of intermediate F2 (670 mg; 2.21 mmol) and HCl [3M] in CPME (2.2 mL; 6.62 mmol) in MeOH (20 mL) was stirred at rt for 56 h. The mixture was evaporated to dryness to give a residue which was taken-up with Et₂O and pentane and the solvents were evaporated to give 510 mg of a mixture of intermediates F3 and F3' (70/30) as a colorless oil (98%).

Preparation of Intermediate F4/F4'

2,6-Dichloro-3 cyano-5 fluoropyridine (457 mg; 2.39 mmol), DIPEA (2.1 mL; 12.0 mmol), intermediates F3/F3' (510 mg; 2.56 mmol) in THF (6.4 mL) and EtOH (6.4 mL) were heated at 90° C. for 2 h in a sealed tube. Solvents were evaporated. EtOAc was added and the resulting solution was washed twice with water. The organic layer was dried over MgSO₄, filtered, evaporated and purified by preparative LC (Regular SiOH 30 μm, 25 g Interchim, mobile phase gradient: from Heptane/EtOAc 90/10 to 50/50) to give 304 mg of intermediate F4 as a yellow solid (36%), and 76 mg of intermediate F4' as a yellow oil (9%).

Compound F5

Compound F5 was prepared in the same way as the racemate compound C6 starting from compound X and mixture of intermediates F4/F4'

$^1$H NMR (400 MHz, DMSO-$d_6$) δ ppm 0.84 (s, 3 H) 0.89 (s, 3 H) 2.05 (br d, J=7.6 Hz, 2 H) 2.56-2.74 (m, 2 H) 4.88-4.99 (m, 3 H) 5.82 (m, 1 H) 7.52 (br d, J=7.6 Hz, 1 H) 7.84 (d, J=11.1 Hz, 1 H) 8.32 (d, J=3.0 Hz, 1H) 8.33 (t, J=3.0 Hz, 1 H) 8.97 (d, J=2.0 Hz, 1 H) 12.09 (br s, 1 H) 12.45 (br s, 1 H). LC-MS Mass Found [M+H]+=442.1. Rt(min)=2.60 (method A), mp° C.=257.3 & 263.62.

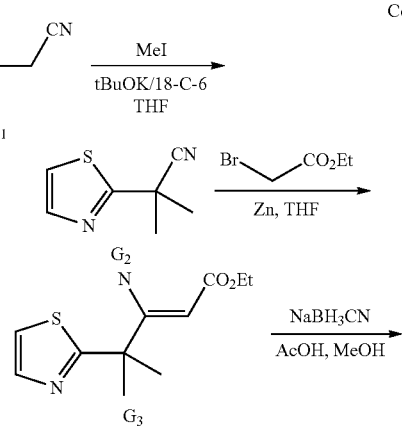

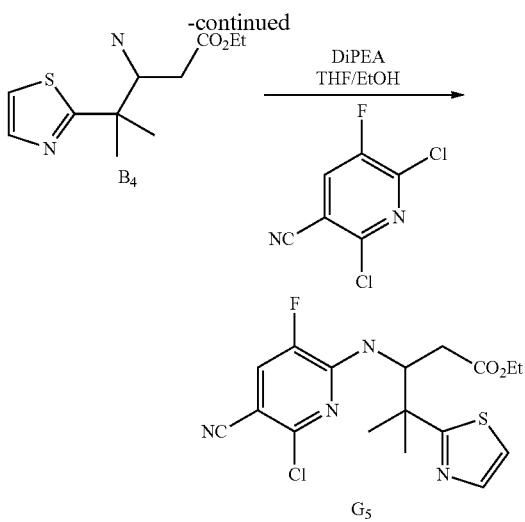

Preparation of Intermediate G2 tBuOK (4.74 g, 42.3 mmol) was added to a solution of compound G1 [101010-74-6] (2.10 g, 16.9 mmol) in THF (65 mL), at 0° C. 18-Crown-6 (0.670 g, 2.50 mmol) was added to the mixture. The mixture was stirred at 0° C. for 15 minutes and iodomethane (2.57 mL, 50.7 mmol) was added dropwise at 0° C. The reaction mixture was stirred at 0° C. for 15 minutes then at rt overnight. An aqueous saturated solution of $NH_4Cl$ was added. The reaction mixture was extracted with ethyl acetate (2×150 mL), dried over $Na_2SO_4$, filtered and concentrated under reduced pressure. The residue was purified by preparative LC (irregular SiOH, 40-63 μm, Fluka, liquid loading (DCM), mobile phase: cyclohexane/EtOAc gradient: from 90/10 to 70/30) to give 1.64 g of intermediate G2 as a yellow liquid (64%).

Preparation of Intermediate G3

Methanesulfonic acid (0.260 mL, 4.00 mmol) was added to a suspension of activated Zn (3.43 g, 52.5 mmol) in THF (24 mL) at rt. The reaction mixture was stirred at reflux for 15 minutes and a solution of intermediate G2 (1.60 g, 10.5 mmol) in THF (8 mL) was added. Then a solution of ethylbromoacetate (3.50 mL, 31.5 mmol) in THF (16 mL) was added dropwise at reflux. The reaction mixture was stirred at reflux for 1 h. An aqueous saturated solution of $NaHCO_3$ was added and the mixture was filtered over celite. The filtrate was extracted with ethyl acetate (2×15 mL), dried over Na2SO4, filtered and concentrated under reduced pressure and the residue was purified by preparative LC (irregular SiOH, 40-63 μm, Fluka, liquid loading (DCM), mobile phase: cyclohexane/EtOAc 8/2) to give 1.90 g of intermediate G3 as a colorless liquid (75%).

Preparation of Intermediate G4

To a solution of intermediate G3 (1.89 g; 7.86 mmol) in MeOH (73 mL) and AcOH (20.5 mL) was added a commercial solution of $NaBH_3CN$ 1M in THF (18.9 mL; 18.9 mmol) dropwise at rt. The reaction mixture was stirred at rt for 16 h. The mixture was evaporated to dryness and the residue was co-evaporated with toluene to give a white gum. Then the residue was taken up in water, an aqueous solution of NaOH (1M) was added and the aqueous layer was extracted with DCM (3×). The combined organic layers were dried over $MgSO_4$ and concentrated to give 1.7 g of crude G4.

The oil was purified by preparative LC (Irregular SiOH 15-40 μm, 50 g Merck, mobile phase gradient: from DCM/ MeOH: 100/0 to 90/10) to give 583 mg of intermediate G4 as a colorless oil (31%).

Preparation of Intermediate G5

2,6-Dichloro-3 cyano-5 fluoropyridine (429 mg; 2.24 mmol), DIPEA (2 mL; 11.4 mmol), intermediate G4 (582 mg; 2.40 mmol) in THF (6 mL) and EtOH (6 mL) were heated at 90° C. for 2 h in a sealed tube. Solvents were evaporated. EtOAc was added and the resulting mixture was washed twice with water. The organic layer was dried over $MgSO_4$, filtered, evaporated in vacuo and purified by preparative LC (Regular SiOH 30 μm, 40 g Interchim, mobile phase gradient: from Heptane/EtOAc: 90/10 to 50/50) to give 500 mg of intermediate G5 as a beige solid (56%).

Compound G6

Compound G6 was prepared in the same way as the racemate compound C6 starting from compound X and intermediate G5

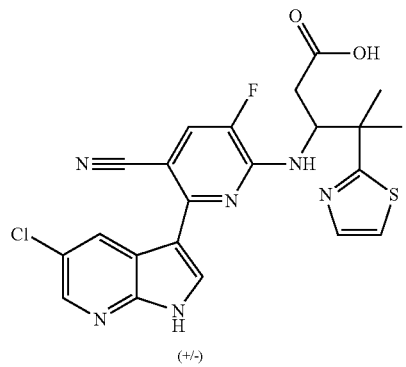 [SMILES: CC(C)(c1nccs1)C(CC(=O)O)Nc1nc(-c2c[nH]c3ncc(Cl)cc23)c(C#N)cc1F]

$^1$H NMR (400 MHz, DMSO-$d_6$) δ ppm 1.33 (s, 3 H) 1.45 (s, 3 H) 2.42 (br d, J=14.7 Hz, 1 H) 2.62 (dd, J=15.7, 11.1 Hz, 1 H) 5.45 (br t, J=9.9 Hz, 1 H) 7.58 (d, J=3.0 Hz, 1 H) 7.60-7.71 (m, 1 H) 7.67 (d, J=3.0 Hz, 1 H) 7.88 (d, J=11.6 Hz, 1 H) 8.31 (d, J=2.5 Hz, 1 H) 8.34 (d, J=2.0 Hz, 1 H) 9.02 (d, J=2.5 Hz, 1 H) 12.11 (br s, 1 H) 12.45 (br s, 1 H). LC-MS Mass Found [M+H]+=485. Rt(min)=2.24 (method A), mp° C.=263.9.

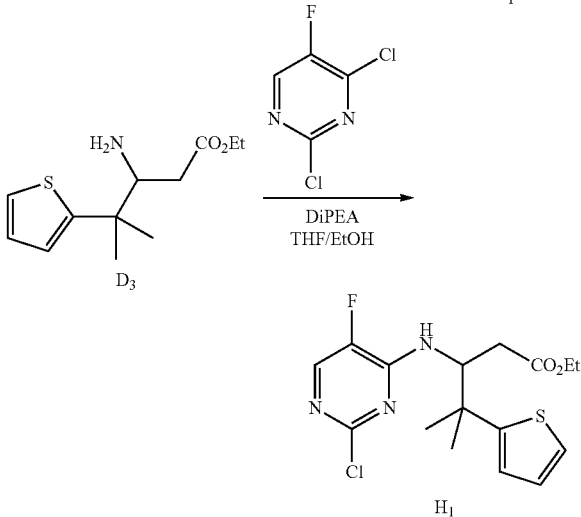

Preparation of Intermediate H1

In sealed tube, a solution of 2,4-dichloro-5-fluoro-pyrimidine (318 mg; 1.91 mmol), intermediate D3 (460 mg; 1.91 mmol) and DIPEA (1.6 mL; 9.53 mmol) in THF (10 mL) and EtOH (10 mL) was stirred at 80° C. overnight. The mixture was evaporated until dryness, the residue was solubilized in EtOAc, then water was added and the layers were separated. The organic layer was washed with brine (once), dried over MgSO$_4$, filtered, concentrated in vacuo and purified by preparative LC (Irregular SiOH 15-40 μm, 30 g Merck, liquid loading, mobile phase gradient: from Heptane/DCM 50:50 to 80:20). The fractions containing product were combined and the solvent was removed in vacuo to give 338 mg of intermediate H1 as a yellow solid (48%).

Compound H2

Compound H2 was prepared in the same way as the racemate compound C6 starting from compound X and intermediate H1 except the final saponification was performed with KOH (10eq) in a mixture of EtOH/H$_2$O at rt.

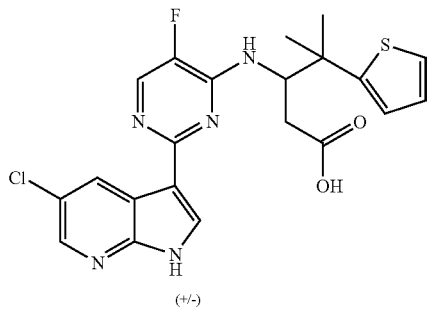 [SMILES: CC(C)(c1cccs1)C(CC(=O)O)Nc1nc(-c2c[nH]c3ncc(Cl)cc23)ncc1F]

(+/-)

$^1$H NMR (400 MHz, DMSO-d$_6$) δ ppm 1.31 (s, 3 H) 1.41 (s, 3 H) 2.25 (br d, J=16.7 Hz, 1 H) 2.50 (m, 1 H) 5.12-5.32 (m, 1 H) 6.97 (m, 1 H) 7.04 (m, 1 H) 7.30-7.96 (m, 1 H)7.39 (d, J=5.1 Hz, 1 H) 8.16 (d, J=3.5 Hz 1 H) 8.19 (s, 1H) 8.30 (d, J=2.5 Hz, 1 H) 8.93 (s, 1 H) 12.04 (br s, 1 H) 12.31 (br s, 1 H). LC-MS Mass Found [M+H]+=460. Rt(min)=2.36 (method A), mp° C.=175.6 & 228.74.

Synthesis of Compound I3

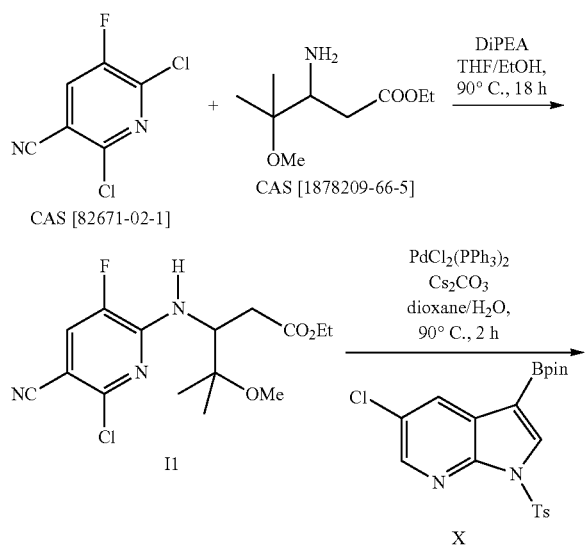

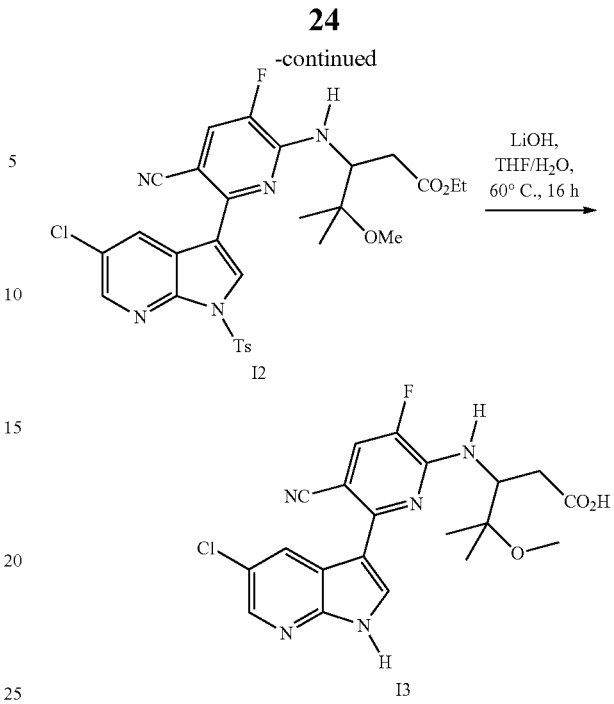

Preparation of Intermediate I1

2,6-dichloro-3 cyano-5 Fluoropyridine (0.23 g; 1.2 mmol), Diisopropylethylamine (1.1 mL; 6.1 mmol), ethyl 3-amino-4-methoxy-4-methylpentanoate (CAS [1878209-66-5], 0.23 g; 1.2 mmol) in THF (3.0 mL) and EtOH (3.0 mL) were heated at 90° C. for 18 hours in a sealed tube. EtOAc was added and washed twice with brine. The organic layer was dried over MgSO$_4$, filtered and evaporated in vacuo to give a colorless oil. It was purified by preparative LC (regular SiOH 30 μm, 24 g, mobile phase gradient: from Heptane/AcOEt 80/20 to 70/30) to give 0.195 g of intermediate I1 as a white solid (47%).

Preparation of Intermediate I2

Under N2, in a sealed tube, a mixture of X (144 mg; 0.33 mmol), I1 (95 mg; 0.28 mmol) and cesium carbonate (0.32 g; 0.97 mmol) in 1,4-dioxane (2.4 mL) and water (0.75 mL) was degassed with N$_2$ for 5 min. PdCl$_2$(PPh$_3$)$_2$ (19 mg; 28 μmol) was added and the reaction mixture was degassed again with N$_2$ for 2 min. The reaction mixture was heated at 90° C. for 2 hours. The reaction mixture was cooled down to room temperature. DCM and brine were added to reaction mixture. The aqueous layer was extracted with DCM. The combined organic layers were washed dried over MgSO$_4$, filtered off and concentrated to dryness to afford the crude compound. It was purified by preparative LC (regular SiOH 30 μm, 12 g, dry loading, mobile phase gradient: from Heptane/EtOAc 90/10 to 70/30) to give 81 mg of intermediate I2 as a white solid (48%).

Preparation of Compound I3

A solution of Lithium hydroxide monohydrate (28 mg, 0.66 mmol) in water (0.25 mL) was added to a mixture of I2 (81 mg, 0.13 mmol) in THF (0.73 mL). The mixture was stirred for 18 hours at 60° C.

The solution was evaporated in vacuo and purified by preparative LC (regular SiOH 30 μm, 12 g, mobile phase gradient: from DCM/MeOH/Acetic acid 99/1/0.1 to 95/5/0.5) to give after evaporation a fraction which was freeze-dried in MeCN/H$_2$O to give 37 mg of compound I3 as a white solid (65%, m.p.=275° C.).

1H NMR (400 MHz, DMSO-d6) δ ppm 1.07 (s, 3 H) 1.12 (s, 3 H) 2.61-2.72 (m, 2 H) 3.15 (s, 3 H) 5.14 (dt, J=9.6; 2.0 Hz, 1 H) 7.57 (br d, J=8.6 Hz, 1 H) 7.86 (d, J=11.1 Hz, 1 H) 8.31 (s, 1H) 8.32 (s, 1 H) 8.97 (d, J=2.0 Hz, 1 H) 11.7-12.4 (m, 1 H) 12.45 (br s, 1 H)

Synthesis of Compound J3

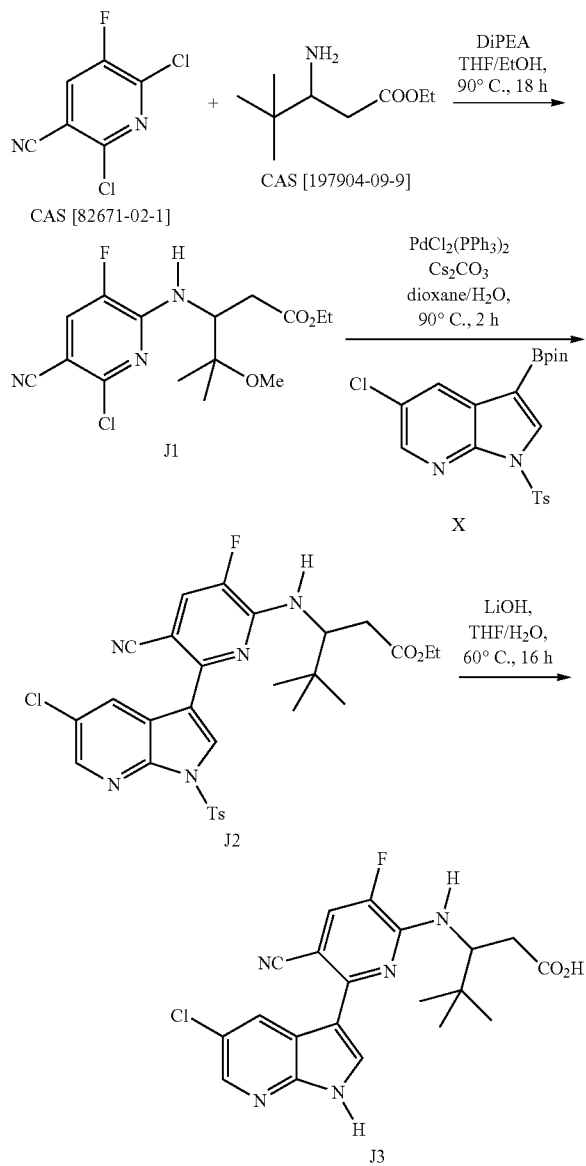

Preparation of intermediate J1

2,6-dichloro-3 cyano-5 Fluoropyridine (1 g; 5.24 mmol), Diisopropylethylamine (4.5 mL; 26.2 mmol), ethyl 3-amino-4,4-dimethylpentanoate (CAS [197904-09-9], 1.09 g; 6.28 mmol) in THF (13 mL) and EtOH (13 mL) were heated at 90° C. for 18 hours in a sealed tube. EtOAc was added and washed twice with brine. The organic layer was dried over MgSO$_4$, filtered and evaporated in vacuo to give 2.4 g as a yellow oil. It was purified by preparative LC (irregular SiOH 15-40 µm, 80 g Grace, dry loading (on SiOH), mobile phase gradient: from Heptane/etOAc 95/5 to 50/50) to give 1.33 g of intermediate J1 as a yellow solid (77%).

Preparation of Intermediate J2

Under N2, in a sealed tube, a mixture of X (250 mg; 0.578 mmol), J1 (246 mg; 0.751 mmol) and cesium carbonate (0.659 g; 2.02 mmol) in 1,4-dioxane (11 mL) and water (3 mL) was degassed with N$_2$ for 5 min. PdCl$_2$(PPh$_3$)$_2$ (41 mg; 58 µmol) was added and the reaction mixture was degassed again with N$_2$ for 2 min. The reaction mixture was heated at 90° C. for 1 hour. The reaction mixture was cooled down to room temperature. DCM and brine were added to reaction mixture. The aqueous layer was extracted with DCM. The combined organic layers were washed dried over MgSO$_4$, filtered off and concentrated to dryness to afford the crude compound. It was purified by preparative LC (irregular SiOH 15-40 µm, 10 g, dry loading (on SiOH), mobile phase gradient: from Heptane/EtOAc 95/5 to 70/30) to give 142 mg of intermediate J2 as a pale green solid (41%).

Preparation of Compound J3

To a solution of J2 (142 mg; 237 µmol) in water (3.7 mL) was added Sodium hydroxide 3M in H$_2$O (475 µL; 1.42 mmol). The reaction mixture was stirred at room temperature for 16 hours. Solvent was evaporated in vacuo and the residue was taken up in water. An aqueous solution of HCl (1N) was added until pH=1. The precipitate formed was filtered off, washed with water and dried under vacuum to afford 69 mg of a beige solid.

It was triturated into MeOH/H$_2$O/DMSO (5/2/3 mL) and sonicated. The precipitate was filtered to give 43 mg of compound J3 (44%,).

1H NMR (500 MHz, DMSO-d6) δ ppm 0.93 (s, 9 H) 2.53-2.71 (m, 2 H) 4.84 (br t, J=9.5 Hz, 1 H) 7.59 (br s, 1 H) 7.83 (d, J=11.4 Hz, 1 H) 8.33 (s, 1H) 8.36 (s, 1 H) 8.99 (s, 1 H) 12.07 (br s, 1 H) 12.47 (br s, 1 H)

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (R$_t$) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| V3018 V3001 | Waters: Acquity UPLC ®-DAD and Quattro Micro ™ | Waters: BEH C18 (1.7 µm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |

Biological Activity of Compounds of Formula (I)

The in vitro antiviral activity of the compounds was determined using a cell-based antiviral assay. In this assay, the cytopathic effect (CPE) in Madin-Darby canine kidney (MDCK) cells infected by influenza virus A/Taiwan/1/86 (H1N1) was monitored in the presence or absence of the compounds. White 384-well microtiter assay plates (Greiner) were filled via acoustic drop ejection using the echo liquid handler (Labcyte, Sunnyvale, Calif.). Two hundred nanoliter of compound stock solutions (100% DMSO) were transferred to the assay plates. MDCK cells were dispensed to the plate at final density of 25,000 or 6,000 cells/well. Then Influenza A/Taiwan/1/86 (H1N1) virus was added at a multiplicity of infection of 0.001 or 0.01, respectively. The wells contain 0.5% DMSO per volume. Virus- and mock-infected controls were included in each test. The plates were incubated at 37° C. in 5% $CO_2$. Three days post-virus exposure, the cytopathic effect was quantified by measuring the reduction in ATP levels using the ATPlite™ kit (PerkinElmer, Zaventem, Belgium) according to the manufacturer's instructions. The $IC_{50}$ was defined as the 50% inhibitory concentration. In parallel, compounds were incubated for three days in white 384-well microtiter plates and the in vitro cytotoxicity of compounds in MDCK cells was determined by measuring the ATP content of the cells using the ATPlite™ kit (PerkinElmer, Zaventem, Belgium) according to the manufacturer's instructions. Cytotoxicity was reported as $CC_{50}$, the concentration that causes a 50% reduction in cell viability.

| Structural formula | FLU-AVE-MDCK-ATP-TW_EC50 | FLU-AVE-MDCK-ATP-TW_pEC50 |
|---|---|---|
| | 0.00057 | 9.2 |
| | 0.002542 | 8.6 |
| | 0.000267 | 9.6 |

-continued

| Structural formula | FLU-AVE-MDCK-ATP-TW_EC50 | FLU-AVE-MDCK-ATP-TW_pEC50 |
|---|---|---|
| | 0.002558 | 8.6 |
| | 0.982291 | 6.0 |
| | 0.001 | 9.0 |
| | 0.00047 | |
| | 1.89 | |

| Structural formula | FLU-AVE-MDCK-ATP-TW_EC50 | FLU-AVE-MDCK-ATP-TW_pEC50 |
|---|---|---|
| 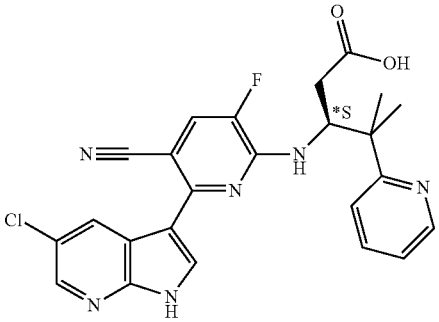 | 0.000075 | 11.2 |
| 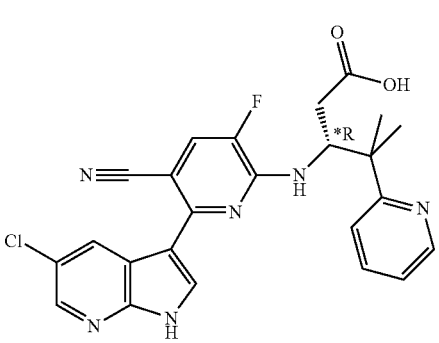 | 0.0054 | 8.3 |

The invention claimed is:

1. A compound of formula (I)

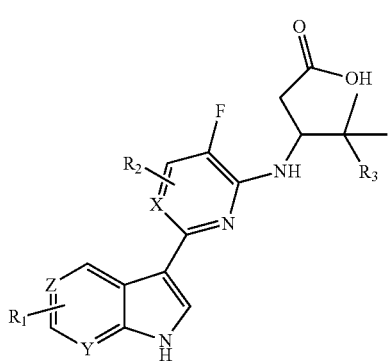

a stereo-isomeric form, a pharmaceutically acceptable salt, solvate or polymorph thereof, wherein Y is N, X is C or N, Z is C or N, $R_1$ is halogen or H, $R_2$ is H or CN, and $R_3$ is heterocycle or $OCH_3$.

2. A compound according to claim 1 wherein $R_1$ is chloro and $R_3$ is a heterocycle comprising one or more heteroatoms selected from N, O or S, said heterocycle may have 4, 5, 6 or 7 ring atoms and may optionally be substituted by $C_{1-6}$ alkyl.

3. A compound according to claim 1 having the structural formula (II) or (III)

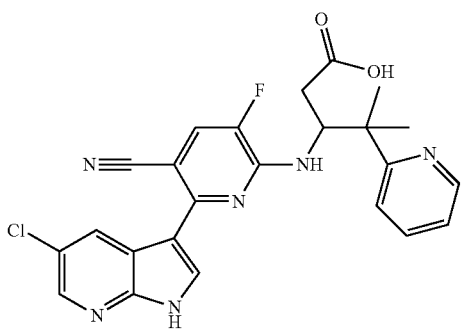

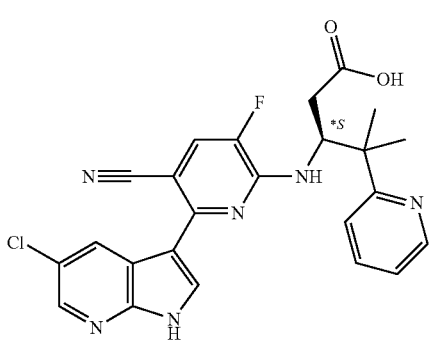

4. A pharmaceutical composition comprising a compound of formula (I) or a stereo-isomeric form, a pharmaceutically acceptable salt, solvate or polymorph thereof according to claim 1 together with one or more pharmaceutically acceptable excipients, diluents or carriers.

5. A method for treating viral influenza infection in a patient in need thereof comprising administering to the patient an effective amount of a compound represented by the following structural formula (I)

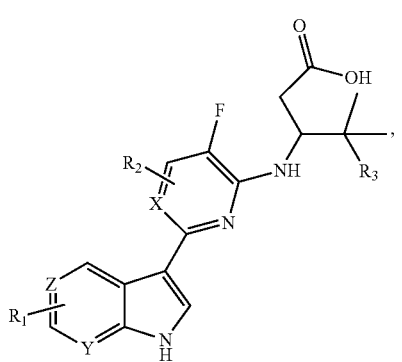

a stereo-isomeric form, a pharmaceutically acceptable salt, solvate or polymorph thereof, wherein Y is N, X is C or N, Z is C or N, R1 is halogen or H, R2 is H or CN, and R3 is heterocycle or OCH3.

6. The method of claim 5 further comprises co-administering to the patient an additional therapeutic agent.

7. The method of claim 6 wherein the additional therapeutic agent is selected from an antiviral agent or influenza vaccine, or both.

8. A compound selected from the group consisting of:

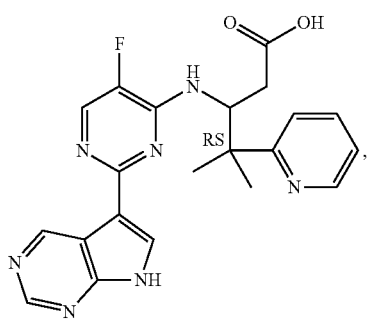

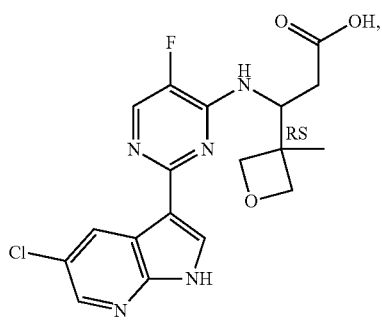

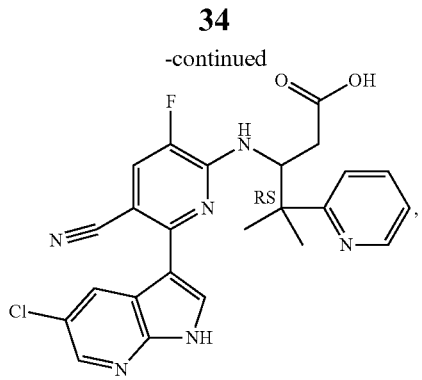

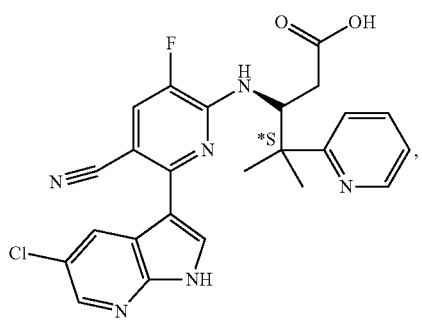

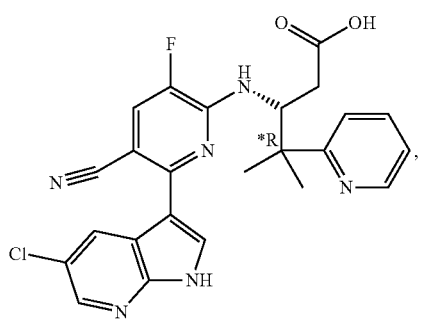

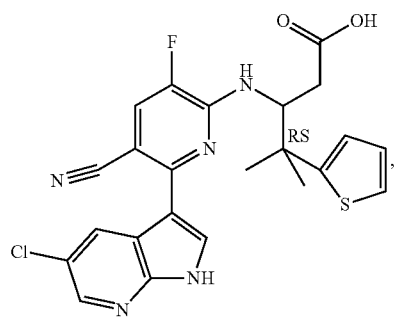

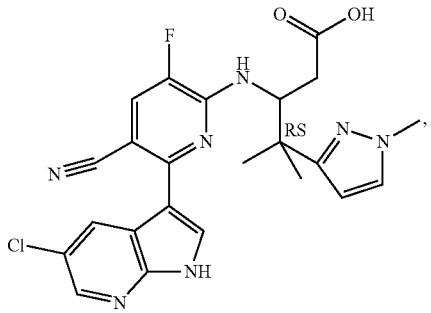
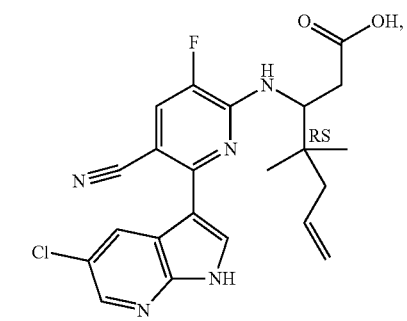
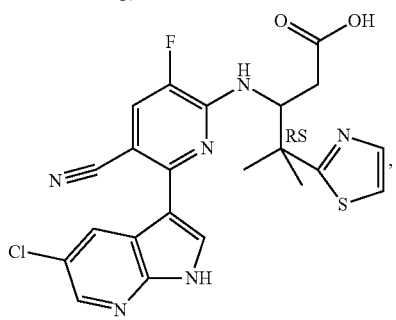
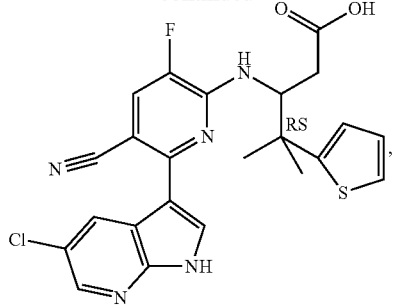
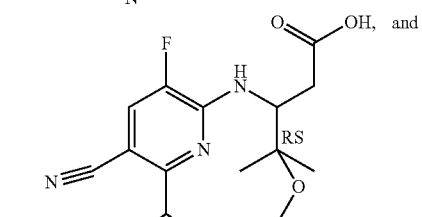
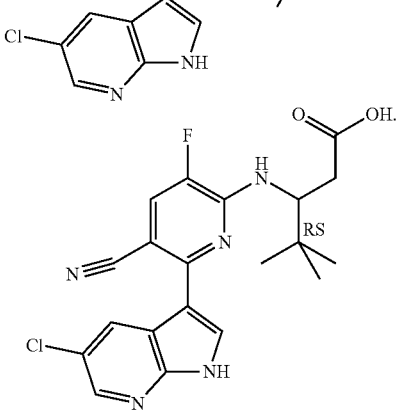
* * * * *